US006388124B2

(12) United States Patent
Takahashi et al.

(10) Patent No.: US 6,388,124 B2
(45) Date of Patent: May 14, 2002

(54) DIHALO-COMPOUND AND PROCESS FOR PRODUCING VITAMIN A DERIVATIVE

(75) Inventors: Toshiya Takahashi, Ibaraki; Shinzo Seko, Toyonaka, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/769,527

(22) Filed: Jan. 26, 2001

(30) Foreign Application Priority Data

Jan. 28, 2000 (JP) ........................... 2000-019975
Mar. 13, 2000 (JP) ........................... 2000-068278
May 9, 2000 (JP) ........................... 2000-135577

(51) Int. Cl.$^7$ .................. C07C 69/62; C07C 69/74; C07C 69/00; C07C 315/00; C07C 35/18; C07C 31/34; C07C 29/00
(52) U.S. Cl. ................. 560/219; 560/128; 560/129; 560/205; 568/28; 568/32; 568/850; 568/824; 568/841
(58) Field of Search ................. 560/219, 128, 560/129, 205; 568/28, 32, 850, 824, 841

(56) References Cited

U.S. PATENT DOCUMENTS

| 4,825,006 A | 4/1989 | Otera et al. |
| 4,876,400 A | 10/1989 | Otera et al. |
| 4,886,916 A | 12/1989 | Onishi et al. |
| 4,947,001 A | 8/1990 | Onishi et al. |
| 5,053,552 A | 10/1991 | Mori et al. |

FOREIGN PATENT DOCUMENTS

| EP | 0900785 | 3/1999 |
| WO | WO0061530 | 10/2000 |

OTHER PUBLICATIONS

Torii et al., Alicyclic Terpenoids From Cyclocitral Phenyl . . . , *Chemistry Letters*, Chemical Society of Japan, 1975, pp. 479–482,.

Mercier et al., Organometallic Chemistry in Industrial Vitamin A and Vitamin E Synthesis, *Pure & Appl. Chem.*, vol. 66, No. 7, 1994, pp. 1509–1518.

Lee et al., Selenium Dioxide Catalyzed Conversion . . . , *J. Org. Chem.*, vol. 53, 1988, pp. 3634–3637.

Labrouillère et al., Bismuth (III) Chloride—Catalyzed . . . , *Synlett*, Sep. 1994, pp. 723–724.

Lissel et al., *Geranyl–chlorid*, Synlett, Apr. 1983, pp. 314–315 (translated portion into English).

*Primary Examiner*—Johann Richter
*Assistant Examiner*—Elvis O. Price
(74) *Attorney, Agent, or Firm*—Birch, Stewart, Kolasch & Birch, LLP

(57) ABSTRACT

There is disclosed a dihalo-compound of formula (1):

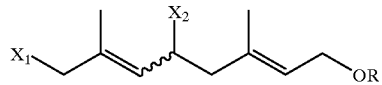

(1)

wherein
 $X_1$ and $X_2$ represent different halogen atoms,
 R represents a hydrogen atom or a protective group for a hydroxyl group, and a process for producing vitamin A derivative via a sulfone derivative of formula (5):

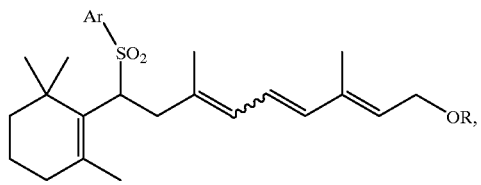

(5)

wherein Ar represents an optionally substituted aryl group, and R represents the same as defined above.

21 Claims, No Drawings

DIHALO-COMPOUND AND PROCESS FOR PRODUCING VITAMIN A DERIVATIVE

FIELD OF THE INVENTION

The present invention relates to a dihalo-compound which useful as an intermediate producing for retinol and the like, and a process for producing the same.

BACKGROUND OF THE INVENTION

There have been known a method for producing vitamin A by a carbon-increment reaction at the side chain of β-ionone (C13) (Pure & Appl. Chem. 66, 1509, (1994)) and a process of coupling C10 sulfones with C10 aldehydes, and eliminating a sulfone group (JP-B 4-3388, JP-B 5-61265 and the like). However, β-ionone (C13) is very expensive and an expensive acetaldehyde derivative is required as an oxidizing agent in a step of preparing said C10 aldehyde.

SUMMARY OF THE INVENTION

According to the present invention, vitamin A can be industrially advantageously produced in a good yield using a dihalo-compound, which can be readily derived from economically available linalool or geraniol, and The present invention provides:
1. a dihalo-compound of formula (1):

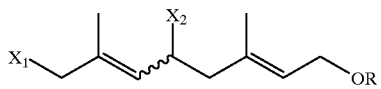

(1)

wherein
$X_1$ and $X_2$ represent different halogen atoms,
R represents a hydrogen atom or a protective group for a hydroxyl group, and the wavy line denoted by "〜" means that the stereochemistry relating to the double bond to which said wavy line is bonded is E, Z or a mixture thereof, 2. a method for producing a dihalo-compound of formula (1) as defined above, which comprises
reacting at least one compound selected from an alcohol compound of formula (2):

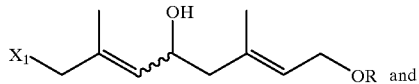

(2)

and
an alcohol compound of formula (3):

(3)

with a halogenating agent having a halogen atom represented by $X_2$ as defined in connection with formula (1) above,
wherein in formulae (2) and (3) $X_1$ represents a halogen atom, R represents a protective group for a hydroxy group, and the wavy line denoted by "〜" means that the stereochemistry relating to the double bond to which said wavy line is bonded is E, Z or a mixture thereof, and 3. a method for producing a sulfone derivative of formula (5):

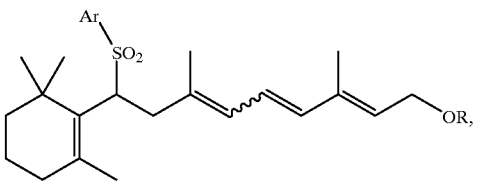

(5)

wherein
Ar represents an optionally substituted aryl group,
R represents a hydrogen atom or a protective group for a hydroxy group, and the wavy line denoted by "〜" means that the stereochemistry relating to the double bond to which said wavy line is bonded is E, Z or a mixture thereof,
which comprises
reacting a sulfone compound of formula (6):

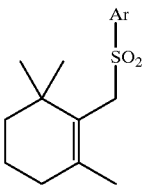

(6)

wherein Ar is the same as defined above, with a dihalo-compound of formula (1):

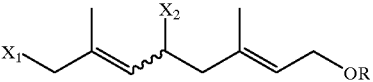

(1)

wherein $X_1$ and $X_2$ represent different halogen atoms and the wavy line denoted by "〜" means that the stereochemistry relating to the double bond to which said wavy line is bonded is E, Z or a mixture thereof, in the presence of a base.

DETAILED DESCRIPTION

The present invention will be explained in detail below.

$X_1$ and $X_2$ represent different halogen atoms. Examples of a halogen atom represented by $X_1$ or $X_2$ in the formulae of the present invention include a chlorine atom, a bromine atom, and an iodine atom. $X_1$ preferably represents a bromine atom, and $X_2$ preferably represents a chlorine atom.

Examples of the protecting group for a hydroxy group represented by R include
an acyl group such as formyl, acetyl, ethoxyacetyl, fluoroacetyl, difluoroacetyl, trifluoroacetyl, chloroacetyl, dichloroacetyl, trichloroacetyl, bromoacetyl, dibromoacetyl, tribromoacetyl, propionyl, 2-chloropropionyl, 3-chloropropionyl, butyryl, 2-chlorobutyryl,3-chlorobutyryl,4-chlorobutyryl, 2-methylbutyryl, 2-ethylbutyryl, valeryl, 2-methylvaleryl, 4-methylvaleryl, hexanoyl, isobutyryl, isovaleryl, or pivaloyl group,
a benzoyl, o-chlorobenzoyl, m-chlorobenzoyl, p-chlorobenzoyl, o-hydroxybenzoyl, m-hydroxybenzoyl, p-hydroxybenzoyl, o-acetoxybenzoyl, o-methoxybenzoyl, m-ethoxybenzoyl, p-methoxybenzoyl, p-nitrobenzoyl group or the like, a silyl group such as trimethylsilyl, triethylsilyl, t-butyldimethylsilyl, t-butyldiphenylsilyl or the like, an alkoxyalkyl group such as methoxymethyl, methoxyethoxymethyl, 1-ethoxyethyl or the like, a tetrahydropyranyl group and the like, a benzyl group, a p-methoxybenzyl group, a t-butyl group, a trityl group, a 2,2,2-trichloroethoxycarbonyl group, allyloxycarbonyl group and the like.

Examples of the halogenating agent having a halogen atom represented by $X_2$ as defined in connection with formula (1) above include a halide of a transition metal of Group 4, a halide of sulfur and a halide of phosphorus.

Said halide of a transition metal of Group 4 include a halide of formula (4):

$$M(X_2)_a(OR')_{4-a} \qquad (4)$$

wherein M is a transition metal of Group 4, "a" is an integer of 1 to 4 and R' is a straight or branched chain alkyl group having 1 to 5 carbon atoms.

Examples of the metal atom "M" in the halide (4) of a transition metal of Group 4 include titanium, zirconium and hafnium. In particular, a titanium is preferred among them.

Examples of the linear or branched alkyl group having a carbon number of 1 to 5 represented by R' in formula (4) include a methyl, ethyl, n-propyl, iso-propyl, n-butyl, s-butyl, t-butyl and n-pentyl group. Specific examples of the halide of a transition metal of Group 4 represented by formula (4) include titanium tetrachloride, titanium tetrabromide, dichlorotitanium diisopropoxide, zirconium tetrachloride, hafnium tetrachloride and the like.

Examples of the halide of sulfur is thionyl chloride and examples of the halide of phosphorus include phosphorus oxychloride, phosphorus trichloride and phosphorus pentachloride.

An amount of the halogenating agent to be used is usually around 0.25 to 2 moles, preferably around 0.5 to 1.1 moles per mol of the total amount of the alcohols (2) and (3).

The halide of sulfur or phosphorus is preferably used in the presence of a base. The base is not particularly limited and includes an organic amine base and inorganic bases.

Specific examples thereof include pyridine, 4-dimethylaminopyridine, 3-ethyl-4-methylpyridine, 5-ethyl-2-methylpyridine, imidazole, 2-methylimidazole, 3-methylimidazole, 2-ethyl-4-methylimidazole, DBU(1,8-diazabicyclo[5.4.0]undec-7-ene), trimethylamine, triethylamine, dimethylethylamine, methyldiethylamine, t-butyldimethylamine, sodium hydroxide, potassium hydroxide, sodium carbonate, potassium carbonate, sodium bicarbonate, potassium bicarbonate and the like. An amount of the base to be used is usually around 1 to 2 moles per mol of the alcohols (2) or (3).

The reaction is usually conducted in an organic solvent and examples of the solvent include an ether solvent such as diethyl ether, tetrahydrofuran, 1,4-dioxane, dimethoxyethane, anisole and the like, a hydrocarbon solvent such as n-hexane, cyclohexane, n-pentane, benzene, toluene, xylene and the like, a halogenated solvent such as chloroform, dichloromethane, 1,2-dichloroethane, monochlorobenzene, o-dichlorobenzene and the like, and an aprotic polar solvent such as acetonitrile, N,N-dimethylformamide, dimethyl sulfoxide, N,N-dimethylacetamide, hexamethylphosphoric triamide and the like.

The halide of a transition metal of Group 4 is preferably used, together with an ether solvent, and dimethoxyethane is more preferable. These may be used alone or as a mixed solvent thereof. A reaction temperature can be optionally set at a range of −78° C. to a boiling point of a solvent, preferably a range of around −20 to 60° C.

A dihalo-compound of formula (1), wherein $X_1$ is a bromine atom and $X_2$ is a chlorine atom is preferred.

After completion of the reaction, the dihalo-compound (1) can be obtained by conventional post-treatment procedures. It may be purified by extraction, washing, various chromatographies or the like, if necessary.

Next, a description will be made to the method for producing a sulfone derivative of formula (5) as defined above which method comprises reacting a sulfone compound of formula (6) as defined above, with a dihalo-compound of formula (1) in the presence of a base.

Examples of the base to be used include an alkali metal alkoxide, an alkali metal hexamethyldisilazane, a hydride of an alkali metal, an alkyl lithium, a Grignard reagent. Specific examples thereof include sodium methoxide, potassium methoxide, sodium ethoxide, potassium ethoxide, potassium t-butoxide, sodium t-butoxide, sodium hexamethyldisilazane, potassium hexamethyldisilazane, sodium hydride, potassium hydride, n-butyllithium, s-butyllithium, t-butyllithium, ethylmagnesium bromide, ethylmagnesium chloride, methylmagnesium bromide, ethylmagnesium chloride, iso-propylmagnesium bromide, iso-propylmagnesium chloride and the like. Preferred are the alkali metal alkoxide and the alkali metal hexamethyldisilazane.

An amount of the base to be used is usually around 1 to 5 moles, preferably around 1 to 3 moles per mol of the dihalo-compound of formula (1).

The reaction is usually conducted in an organic solvent, and examples thereof include aprotic polar solvents such as N,N-dimethylformamide, dimethyl sulfoxide, N,N-dimethylacetamide, acetonitrile, hexamethylphosphoric triamide and the like, hydrocarbon solvents such as n-hexane, n-heptane, cyclohexane, n-pentane, toluene, xylene and the like, and ether solvents such as diethyl ether, tetrahydrofuran, 1,4-dioxane, anisole, a mixture thereof and the like. Preferred are aprotic polar solvents.

The reaction temperature can be optionally set usually in a range of −78° C. to a boiling point of a solvent used, depending upon the base employed.

After completion of the reaction, the sulfone derivative of formula (5) may be isolated by a usual post-treatment such as extraction, phase separation, washing or the like.

The sulfone derivative of formula (5) thus formed can be further reacted with a base, optionally followed by deprotecting or protecting to produce vitamin A derivative of formula (7):

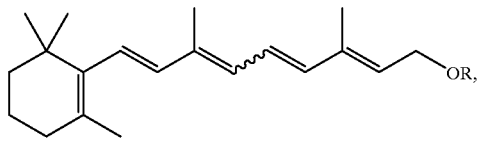

(7)

wherein R and the wavy line have the same meanings as defined above.

The reaction mixture which has resulted from the reaction of the sulfone compound of formula (6) with a base and contains the sulfone derivative of formula (5) may be contacted as it is, without being subjected to a post-treatment, with the base. For example, said method of contacting of the reaction mixture containing the sulfone derivative (5) with a base include one-pot process in which said contacting is carried out in the same reactor as used for producing the sulfone derivative of formula (5).

Alternatively, the sulfone derivative of formula (5) may be isolated and further reacted with a base to produce the vitamin A derivative of formula (7).

Examples of the base to be used include an alkali metal hydroxide, alkali metal hydride and an alkali metal alkoxide. Specific examples thereof include sodium hydroxide, potassium hydroxide, sodium hydride, potassium hydride, sodium methoxide, potassium methoxide, sodium ethoxide, potassium ethoxide, sodium t-butoxide, potassium t-butoxide and the like. Preferred examples of the base to be used include said alkali metal hydroxide and alkali metal alkoxide.

An amount of the base to be used is usually around 1 to 20 moles, preferably around 5 to 15 moles per mole of the sulfone derivative of formula (5).

The reaction temperature is optionally set usually at a range of −40° C. to a boiling point of a solvent used, depending upon a base used in the reaction.

Lower alcohols such as methanol, ethanol, 2-propanol, and t-butanol. may be added to accelerate the progress of the reaction. An amount of an alcohol to be added is usually around 1 to 5 moles per mol of the sulfone derivative (5).

A phase transfer catalyst also may be added in this process to accelerate the reaction.

Examples of the phase transfer catalyst to be used include a quaternary ammonium salt, a quaternary phosphonium salt, a sulfonium salt and the like substituted with at least one group selected from alkyl and aryl group of a carbon number of 1 to 24.

Specific examples of the quaternary ammonium salt include tetramethylammonium chloride, tetraethylammonium chloride, tetrapropylammonium chloride, tetrabutylammonium chloride, tetrapentylammonium chloride, tetrahexylammonium chloride, tetraheptylammonium chloride, tetraoctylammonium chloride, tetrahexadecylammonium chloride, tetraoctadecylammonium chloride, benzyltrimethylammonium chloride, benzyltriethylammonium chloride, benzyltributylammonium chloride, 1-methylpyridinium chloride, 1-hexadecylpyridinium chloride, 1,4-dimethylpyridinium chloride, tetramethyl-2-butylammonium chloride, trimethylcyclopropylammonium chloride, tetramethylammonium bromide, tetraethylammonium bromide, tetrapropylammonium bromide, tetrabutylammonium bromide, tetrapentylammonium bromide, tetrahexylammonium bromide, tetraheptylammonium bromide, tetraoctylammonium bromide, tetrahexadecylammonium bromide, tetraoctadecylammonium bromide, benzyltrimethylammonium bromide, benzyltriethylammonium bromide, benzyltributylammonium bromide, 1-methylpyridinium bromide, 1-hexadecylpyridinium bromide, 1,4-dimethylpyridinium bromide, tetramethyl-2-butylammonium bromide, trimethylcyclopropyl ammonium bromide, tetramethylammonium iodide, tetrabutylammonium iodide, tetraoctylammonium iodide, t-butylethyldimethylammonium iodide, tetradecyltrimethylammonium iodide, hexadecyltrimethylammonium iodide, octadecyltrimethylammonium iodide, benzyltrimethylammonium iodide, benzyltriethylammonium iodide, benzyltributylammonium iodide and the like.

Examples of the quaternary phosphonium salt include tributylmethylphosphonium chloride, triethylmethylphosphonium chloride, methyltriphenoxyphosphonium chloride, butyltriphenylpyosphonium chloride, tetrabutylphosphonium chloride, benzyl triphenylphosphonium chloride, hexadecyldimethylethylphosphonium chloride, tetraphenylphosphonium chloride, tributylmethylphosphonium bromide, triethylmethylphosphonium bromide, methyltriphenoxyphosphonium bromide, butyltriphenylphosphonium bromide, tetrabutylphosphonium bromide, benzyltriphenylphosphonium bromide, hexadecyltrimethylphosphonium bromide, hexadecyltributylphosphonium bromide, hexadecyldimethylethylphosphonium bromide, tetraphenylphosphonium bromide, tributylmethylphosphonium iodide, triethylmethylphosphonium iodide, methylphenoxyphosphonium iodide, butyltriphenylphosphonium iodide, tetrabutylphosphonium iodide, benzyltriphenylphosphonium iodide, hexadecyltrimethylphosphonium iodide and the like.

Examples of the sulfonium salt include dibutylmethylsulfonium chloride, trimethylsulfonium chloride, triethylsulfonium chloride, dibutylmethylsulfonium bromide, trimethylsulfonium bromide, triethylsulfonium bromide, dibutylmethylsulfonium iodide, trimethylsulfonium iodide, triethylsulfonium iodide and the like.

Among the phase transfer catalysts, the quaternary ammonium salt is particularly preferred. An amount of the phase transfer catalyst to be used is usually around 0.01 to 0.2 mole, preferably around 0.02 to 0.1 mole per mol of the dihalo-compound (1).

After the reaction, the vitamin A derivative (7) can be obtained by a conventional post-treatments such as quenching with a saturated aqueous ammonium chloride solution or the like and extraction with an organic solvent, and it may be purified by crystallization, various chromatographies or the like, if necessary.

Deprotected vitamin A derivative (7) is usually obtained in the reaction of the sulfone derivative of formula (5) having an acyl protective group with a base, and it can be protected by subjecting the compound to a protection reaction with an optional protective group, if necessary. For example, vitamin A acetate can be obtained by a conventional method such as the one using acetic anhydride and pyridine or the like.

Alternatively, vitamin A derivative (7) having other protective groups can be subjected to deprotection reaction, if necessary. For example, the silyl protective group may be removed by reacting the compound with tetra-n-butylammonium fluoride, the alkoxyalkyl or tetrahydropyranyl group may be removed by a protonic acid catalyst, and 2,2,2-trichloroethoxycarbonyl can be removed by a reductive deprotection using zinc dust and acetic acid.

Said deprotecting or introducing of the protective groups can be conducted according to the conventional methods as disclosed in "Protective Groups in Organic Synthesis, Greene and Wuts, 2nd Edition (1992), John Wiley & Sons, Inc, the whole disclosure of which is incorporated herein by reference.

Alcohols (2) and (3) can be readily synthesized from linalool or geraniol as shown in the following Scheme 1 (JP-A 11-130730 and JP-A 11-236357). The sulfone compound of formula (6) can be obtained by a process as disclosed in Chemistry Letters 479, (1975). Alcohols (2) and (3) may be an E or Z geometric isomer, or a mixture thereof.

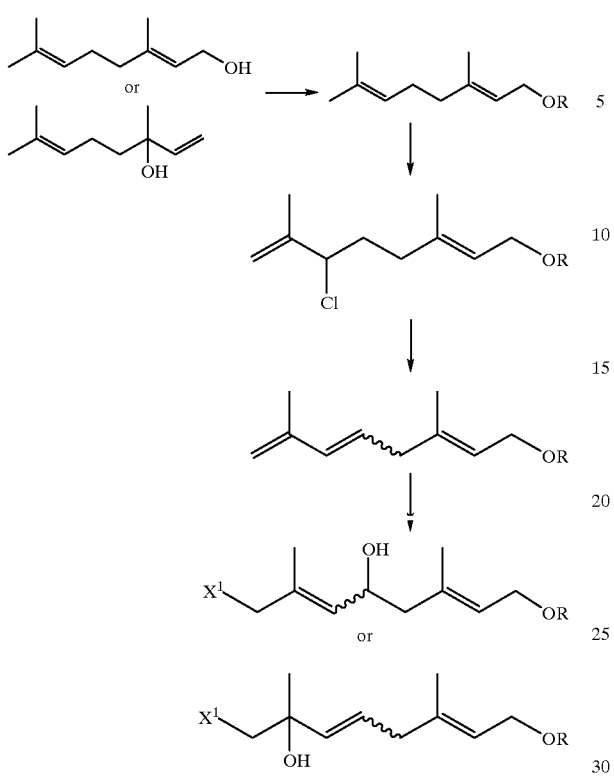

Scheme 1

EXAMPLES

The present invention will be explained in more detail by way of Examples but is not limited to them.

The structures of the compounds used in the Examples are shown below together with notation of (I) to (VIII).

In the following chemical structures, Ts represents a p-tolylsulfonyl group.

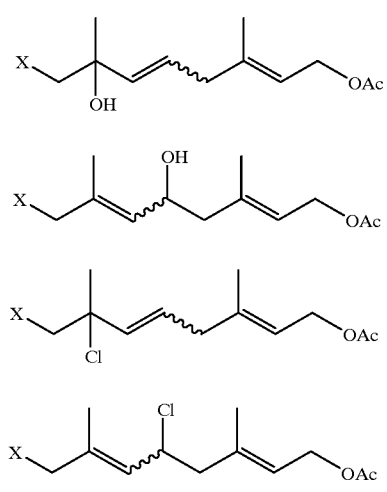

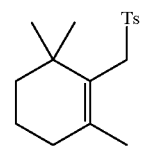

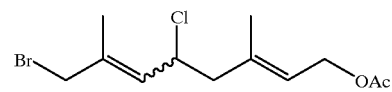

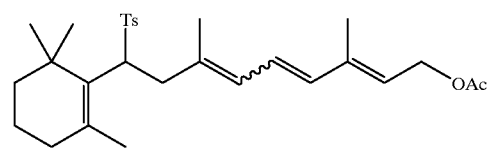

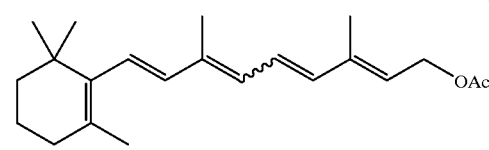

Example 1

To a solution of 0.56 g (1.94 mmol) of an alcohol(I) (X=Br) dissolved in 5 ml of dimethoxyethane was added 1.94 ml of a 1 M solution of titanium tetrachloride (1.94 mmol) in toluene dropwise with a syringe at room temperature under stirring. Thereafter, a temperature was raised to 50° C., the mixture was stirred for 6 hours. After the reaction, the reaction mixture was poured into ice-water, extracted with ethyl acetate. The organic layer was washed with a saturated aqueous sodium chloride solution, dried with anhydrous magnesium sulfate, and the organic solvent was distilled off to give a mixture of 9:91 of dihalocompounds (III) and (IV) (X=Br) as a pale yellow oil in a yield of 93%.

Examples 2–6

An alcohol (1.94 mmol) shown in Table 1 was dissolved in 5 ml of dimethoxyethane, and 1.91 ml of a 1 M solution of titanium tetrachloride (1.94 mmol) in toluene was added dropwise thereto with a syringe at room temperature under stirring, and reacted at 50° C. for 6 hours and the post-treatment was conducted as in Example 1. The results are shown in the following Table 1.

TABLE 1

| Example | Alcohol | X | Product (III)/(IV) ratio | Yield (%) |
|---|---|---|---|---|
| 2 | (II) | Br | 29/71 | 79 |
| 3 | (I)/(II)(7/3) | Br | 13/87 | 85 |
| 4 | (I) | Cl | 9/91 | 91 |
| 5 | (II) | Cl | 46/54 | 90 |
| 6 | (I)/(II)(7/3) | Cl | 26/78 | 90 |

Compounds (IV) (X=Br)

$^1$H-NMR (CDCl$_3$): δ1.72 (3H, s), 1.85 (3H, s), 2.04 (3H, s), 2.45–2.64 (2H, m), 3.92 (2H, s) 4.57 (2H, d, J=7 Hz, 10 Hz), 4.68–4.76(1H, m), 5.43 (1H, t, J-7 Hz), 5.65 (1H, d, J=9 Hz)

$^{13}$C-NMR (CDCl$_3$): δ15.4, 16.8, 21.2, 39.4, 48.6, 55.3, 60.6, 123.1, 130.9, 135.5, 136.9, 171.1

Compound (IV) (X=Cl)

$^1$H-NMR (CDCl$_3$): δ1.72 (3H, s), 1.82 (3H, s), 2.05 (3H, s), 2.44–2.63 (2H, m), 3.99 (2H,s), 4.58 (2H, d, J=7 Hz), 4.68–4.76 (1H, m), 5.43 (1H, t, J=7 Hz), 5.61 (1H, d, J=9 Hz)

$^{13}$C-NMR (CDCl$_3$): δ15.2, 16.9, 21.3, 48.0, 50.9, 55.6, 61.3, 123.3, 130.5, 134.4, 135.7, 171.3

Example 7

0.095 g (0.33 mmol) of a mixture of 70:30 of alcohols (I) and (II) (X=Br) and 27 mg (0.34 mmol) of pyridine were dissolved in 5 ml of hexane, and 41 mg (0.34 mmol) of thionyl chloride was gradually added dropwise thereto at 25° C. under stirring. After the addition, the mixture was stirred at the same temperature for 24 hours. Thereafter, the reaction mixture was poured into 50 ml of ice-water, and the hexane layer was separated. The hexane layer was washed with 10 ml of a 5% aqueous solution of sodium bicarbonate, 20 ml of water and 10 ml of a saturated aqueous solution of sodium chloride, and dried with anhydrous magnesium sulfate. After drying, the solvent was distilled off to obtain a mixture of 42:58 of dihalo-compounds (III) and (IV) (X=Br) as a pale yellow oil in a yield of 84%.

Example 8

The reaction and the post-treatment were conducted as in Example 7 except that alcohols (I) and (II) (X=Cl) were used instead of alcohols (I) and (II) (X=Br). A mixture of 36:64 of dihalo-compounds (III) and (IV) (X=Cl) was obtained as a pale yellow oil in a yield of 84%.

Example 9

To a solution of 0.22 g (2.0 mmol) of potassium t-butoxide dissolved in 8 ml of N,N-dimethylformamide (DMF) and cooled to −40° C. was dropwise added a solution of 0.59 g (2.0 mmol) of the sulfone (V) dissolved in 3 ml of DMF in 15 seconds. Then, the mixture was kept at the same temperature for 5 minutes and, thereafter, cooled to −60° C. After cooling, a solution of 0.34 g (1.0 mmol) of the dihalo-compound (VI) dissolved in 3 ml of DMF was added thereto, and the mixture was stirred at the same temperature for 2 hours. After the reaction, the mixture was quenched with a saturated aqueous ammonium chloride solution, and extracted with ethyl acetate. The resulting organic layer was washed with a saturated aqueous sodium chloride solution, dried with anhydrous magnesium sulfate, and the solvent was distilled off to obtain a crude product containing the sulfone derivative (VII). Liquid chromatography analysis revealed that the yield of sulfone derivative (VII) was 72%.

Example 10

To a solution of 0.33 g (3.0 mmol) of potassium t-butoxide dissolved in 8 ml of N,N-dimethylformamide (DMF) and cooled to −60° C. was dropwise added a solution of 0.59 g (2.0 mmol) of the sulfone (V) dissolved in 3 ml of DMF over 5 minutes, and the resulting mixture was maintained at the same temperature for 1 hour. Then, 3 ml of a solution of 0.34 g (1.30 mmol) of the dihalo-compound (IV) in DMF was added dropwise thereto over 5 minutes, and stirred at the same temperature for 2 hours. After the reaction, the mixture was quenched with a saturated aqueous ammonium chloride solution, and extracted with ethyl acetate. The resulting organic layer was washed with a saturated aqueous sodium chloride solution, dried with anhydrous magnesium sulfate, the solvent was distilled off to obtain a crude product containing the sulfone derivative (VII). The resulting crude product was analyzed by liquid chromatography and the yield of the sulfone derivative (VII) was found to be 95%.

Example 11

To a solution of 0.20 g (0.41 mmol) of a sulfone derivative (VII) dissolved in 10 ml of DMF, 0.16 g (2.9 mmol) of 99% potassium hydroxide was added thereto, and the resulting mixture was stirred at 5° C. for 24 hours. After the reaction, the reaction was poured into a saturated aqueous ammonium chloride solution, and extracted with ethyl acetate. The resulting organic layer was washed successively with a saturated aqueous sodium bicarbonate solution and a saturated sodium chloride solution, dried with anhydrous magnesium sulfate, and the solvent was distilled off to obtain a crude product as a red oil. The hydroxy group of the resulting crude product was acetylated with acetic anhydride and catalytic amount of pyridine. The resulting crude product was analyzed by liquid chromatography and the yield of vitamin A acetate was found to be 87%.

Example 12

Vitamin A acetate was obtained in a yield of 91% in a similar manner as in Example 11 except that 0.03 g (0.41 mmol) of t-butyl alcohol was added.

Example 13

Vitamin A acetate was obtained in a yield of 92% in a similar manner as in Example 11 except that 0.03 g (0.41 mmol) of t-butyl alcohol and 5 mg (0.02 mmol) of benzyltriethylammonium chloride were added.

Example 14

To a solution of 224 mg(2.0 mmol) of potassium t-butoxide dissolved in 8 ml of N,N-dimethylformamide (DMF) and cooled to 0° C. was dropwise added in 20 seconds a solution of 0.58 g (2.0 mmol) of the sulfone (V) dissolved in 4 ml of DMF, and the resulting mixture was maintained at the same temperature for 40 seconds. Then, the reaction mixture was cooled to −60° C., to which was added 4 ml of a solution of 0.35 g (1.0 mmol) of the dihalo-compound (VI) in DMF was added dropwise thereto over 5 minutes, and stirred at the same temperature for 2 hours. After the reaction, 390 mg (7.0 mmol) of 99% potassium hydroxide was added to the mixture and reacted for 20 hours at 20° C. Then the mixture was quenched with a saturated aqueous ammonium chloride solution, and extracted with ethyl acetate. The resulting organic layer was washed with a saturated aqueous sodium chloride solution, dried with anhydrous magnesium sulfate, the solvent was distilled off to obtain a crude retinol as a reddish oil, which was then acetylated with acetic anhydride and catalytic amount of pyridine to give vitamin A acetate. Liquid chromatography analysis showed that the yield was 41% based on the dihalo-compound (VI).

Example 15

Vitamin A acetate was obtained in a yield of 41% based on the dihalo-compound (IV) in a similar manner as in Example 14 except that 10 mg (0.05 mmol) of benzyltriethylammonium chloride was used in addition to 390 mg (7.0 mmol) of 99% potassium hydroxide and reacted at 5° C. for 36 hours.

Example 16

Vitamin A acetate was obtained in a yield of 57% based on the dihalo-compound (IV) in a similar manner as in Example 15 except that 10 mg (0.05 mmol) of benzyltriethylammonium chloride and 65 mg (2 mmol) of methanol was used in addition to 390 mg (7.0 mmol) of 99% potassium hydroxide and reacted at 5° C. for 36 hours.

Example 17

Vitamin A acetate was obtained in a yield of 67% based on the dihalo-compound (VI) in a similar manner as in Example 14 except that 606 mg (15 mmol) of sodium hydroxide was used in place of 390 mg (7.0 mmol) of 99% potassium hydroxide and reacted at 5° C. for 60 hours.

What is claimed is:

1. A dihalo-compound of formula (1):

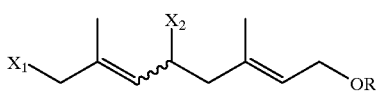

(1)

wherein $X_1$ and $X_2$ represent different halogen atoms,

R represents a hydrogen atom or a protective group for a hydroxyl group, and the wavy line denoted by "∿" means that the stereochemistry relating to the double bond to which said wavy line is bonded is E, Z or a mixture thereof.

2. A dihalo-compound of formula (1) according to claim 1, wherein $X_1$ is a bromine atom and $X_2$ is a chlorine atom.

3. A method for producing a dihalo-compound of formula (1) as defined in claim 1, which comprises reacting at least one compound selected from an alcohol compound of formula (2):

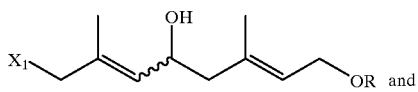

(2)

and an alcohol compound of formula (3):

(3)

with a halogenating agent having a halogen atom represented by $X_2$ as defined in connection with formula (1), wherein in formulae (2) and (3) $X_1$ represents a halogen atom, R represents a protective group for a hydroxy group, and the wavy line denoted by "∿" means that the stereochemistry relating to the double bond to which said wavy line is bonded is E, Z or a mixture thereof.

4. A method according to claim 3, wherein said halogenating agent is a halide of a transition metal of Group 4.

5. A method according to claim 4, wherein said halide of the transition metal of Group 4 is a halide of formula (4):

$$M(X_2)_a(OR')_{4-a} \quad (4)$$

wherein M is a transition metal of Group 4, "a" is an integer of 1 to 4 and R' is a straight or branched chain alkyl group having 1 to 5 carbon atoms.

6. A method according to claim 5, wherein "M" represents titanium.

7. A method according to claim 6, wherein said halide of the transition metal of Group 4 is titanium tetrachloride.

8. A method according to claim 3, reacting of at least one compound selected from said alcohol compound of formula (2) and said alcohol compound of formula (3) with said halogenating agent is carried out in an ether solvent or a mixed solvent thereof.

9. A method according to claim 8, wherein said ether is dimethoxyethane.

10. A method according to claim 3, wherein said halogenating agent is a halogenated sulfur or a halogenated phosphorous.

11. A method according to claim 10, wherein said halogenating agent is thionyl chloride.

12. A method for producing a sulfone derivative of formula (5):

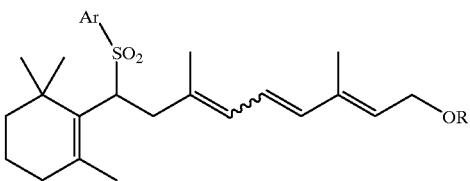

(5)

wherein

Ar represents an optionally substituted aryl group,

R represents a hydrogen atom or a protective group for a hydroxy group, and the wavy line denoted by "∿" means that the stereochemistry relating to the double bond to which said wavy line is bonded is E, Z or a mixture thereof, which comprises reacting a sulfone compound of formula (6):

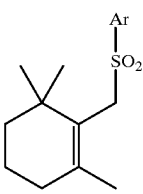

(6)

wherein Ar is the same as defined above, with a dihalo-compound of formula (1):

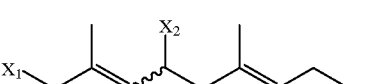

(1)

wherein $X_1$ and $X_2$ represent different halogen atoms and the wavy line denoted by "∿" means that the stereochemistry relating to the double bond to which said wavy line is bonded is E, Z or a mixture thereof, in the presence of a base.

13. A method according to claim 12, wherein said base is an alkali metal alkoxide or alkali metal hexamethyldisilazane.

14. A method according to claim 12 or 13, which further comprises the step of reacting said sulfone derivative of formula (5) with a base to produce vitamin A derivative of formula (7):

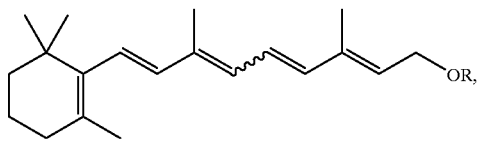

(7)

wherein R and the wavy line have the same meanings as defined in connection with formula (1), optionally followed by a deprotection or protection reaction.

15. A method according to claim 3, which further comprises the steps of:

(a) reacting said dihalo-compound of formula (1) with a sulfone compound of formula (6):

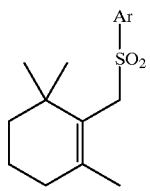

(6)

wherein Ar is an optionally substituted aryl group, in the presence of a base to produce a sulfone derivative of formula (5):

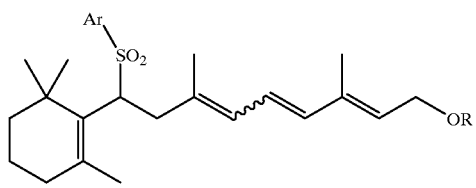

(5)

wherein

Ar represents an optionally substituted aryl group,

R represents a hydrogen atom or a protective group for a hydroxy group, and the wavy line denoted by "〰" means that the stereochemistry relating to the double bond to which said wavy line is bonded is E, Z or a mixture thereof, and (b) reacting said sulfone derivative of formula (5) with a base to produce vitamin A derivative of formula (7):

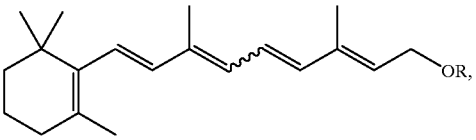

(7)

wherein R and the wavy line have the same meanings as defined above, optionally followed by a deprotection or protection reaction.

16. A method according to claim 15, wherein said base in step (a) is an alkali metal alkoxide or an alkali metal hexamethylsilazane.

17. A method according to claim 14, 15 or 16, wherein the resulting reaction mixture containing said sulfone derivative of formula (5) is contacted with a base selected from an alkali metal alkoxide, an alkali metal hydride and an alkali metal hydroxide.

18. A method according to claim 17, wherein said base is an alkali metal hydroxide or an alkali metal alkoxide.

19. A method according to claim 3, 14 or 15, wherein R represents an acyl group.

20. A method according to claim 19, wherein said acyl group is an acetyl group.

21. A method according to claim 4, 13 or 15, wherein $X_1$ is a bromine atom and $X_2$ is a chlorine atom.

* * * * *